US010040069B2

(12) United States Patent
Moore et al.

(10) Patent No.: US 10,040,069 B2
(45) Date of Patent: Aug. 7, 2018

(54) AMPLIFICATION AND DETECTION OF NUCLEIC ACIDS

(71) Applicants: GENERAL ELECTRIC COMPANY, Schenectady, NY (US); University of Washington, Seattle, WA (US)

(72) Inventors: David Roger Moore, Schenectady, NY (US); Matthew Jeremiah Misner, Delanson, NY (US); Andrew Arthur Paul Burns, Schenectady, NY (US); Joshua Bishop, Seattle, WA (US); Lisa K. Lafleur, Seattle, WA (US); Maxwell Wheeler, Seattle, WA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 227 days.

(21) Appl. No.: 14/807,497

(22) Filed: Jul. 23, 2015

(65) Prior Publication Data
US 2017/0022550 A1    Jan. 26, 2017

(51) Int. Cl.
*C12Q 1/68*     (2018.01)
*C12P 19/34*    (2006.01)
(Continued)

(52) U.S. Cl.
CPC ............. *B01L 7/52* (2013.01); *B01L 3/5023* (2013.01); *B01L 3/502738* (2013.01);
(Continued)

(58) Field of Classification Search
None
See application file for complete search history.

(56) References Cited

U.S. PATENT DOCUMENTS 5,863,502 A * 1/1999 Southgate ............ B01J 19/0046
                                                422/417
5,914,230 A   6/1999 Liu et al.
(Continued)

FOREIGN PATENT DOCUMENTS

WO     2014095931 A1    6/2014

OTHER PUBLICATIONS

Blair et al., "Wax-embedded PCR Reagents," Genome Research, 1994, vol. 4, pp. 191-194.*
(Continued)

*Primary Examiner* — Young J Kim
(74) *Attorney, Agent, or Firm* — GE Global Patent Operation; Pabitra Chakrabarti

(57) ABSTRACT

The present disclosure relates to a sample assessment device. By way of example, the sample assessment device may include a substrate including a sample application region; an amplification region comprising a plurality of amplification reagents; a waste region comprising an entrance fluidically coupled to the amplification region and extending away from the amplification region; and a detection region spaced apart from the amplification region. The sample assessment device may also include a valve coupled to the substrate and configured to separate the amplification region from the detection region in a closed configuration, wherein the amplification region and the valve are positioned on the sample assessment device between the sample application region and the detection region and wherein the sample assessment device is configured to permit lateral flow from the amplification region to the detection region when the valve is in an open configuration.

11 Claims, 6 Drawing Sheets

(51) Int. Cl.
  *B01L 7/00* (2006.01)
  *C12Q 1/6806* (2018.01)
  *C12Q 1/6844* (2018.01)
  *B01L 3/00* (2006.01)

(52) U.S. Cl.
  CPC ......... *C12Q 1/6806* (2013.01); *C12Q 1/6844* (2013.01); *B01L 2200/027* (2013.01); *B01L 2200/10* (2013.01); *B01L 2300/0627* (2013.01); *B01L 2300/0816* (2013.01); *B01L 2300/0864* (2013.01); *B01L 2300/0874* (2013.01); *B01L 2300/0887* (2013.01); *B01L 2300/126* (2013.01); *B01L 2300/18* (2013.01); *B01L 2400/06* (2013.01)

(56) References Cited

U.S. PATENT DOCUMENTS

| | | | |
|---|---|---|---|
| 6,270,965 B1 | 8/2001 | Kleiber et al. | |
| 6,632,399 B1* | 10/2003 | Kellogg | B01F 13/0059 422/505 |
| 8,703,445 B2 | 4/2014 | Collier et al. | |
| 2009/0215050 A1 | 8/2009 | Jenison | |
| 2013/0137054 A1* | 5/2013 | Jiang | C08L 51/10 432/4 |
| 2014/0045221 A1 | 2/2014 | Cai et al. | |
| 2014/0335527 A1 | 11/2014 | Goel | |
| 2015/0010900 A1 | 1/2015 | Eshoo et al. | |

OTHER PUBLICATIONS

Setty et al., Point of Care Technologies for HIV, AIDS Research and Treatment, Jan. 21, 2014, pp. 1-20.

Sin et al., Advances and challenges in biosensor-based diagnosis of infectious diseases, Expert Rev Mol Diagn., Mar. 2014, vol. 14, Issue 2, pp. 225-244.

* cited by examiner

AMPLIFICATION AND DETECTION OF NUCLEIC ACIDS

STATEMENT REGARDING FEDERALLY SPONSORED RESEARCH & DEVELOPMENT

This invention was made with Government support under contract number HR0011-11-2-0007 awarded by DARPA. The Government has certain rights in the invention.

BACKGROUND

The subject matter disclosed herein relates to amplification and detection of nucleic acids using lateral flow devices.

Caregivers may use diagnostic tests to determine if a patient has a particular clinical condition. Such tests may be performed by testing a patient sample (e.g., blood or urine) for the presence of one or more markers such as proteins or small molecules and, depending on their complexity, the tests may be performed in a dedicated testing laboratory or at the point of care, e.g., in the doctor's office or in the field. However, in certain circumstances, a diagnostic test may be a test for the presence of a particular nucleic acid sequence, either sequences in the patient's own genetic material or sequences associated with pathogenic infection. Relative to proteins or small molecule markers, a given nucleic acid sequence may be present in relatively low concentrations in a given biological sample. Accordingly, many techniques for assessing the presence or concentration of a nucleic acid sequence of interest rely on amplification techniques that enrich the sample by amplifying the sequence of interest prior to detection. However, the sample may include inhibitory components and/or inhibitory components may be generated in upstream processes (e.g., cell lysis) that could interfere with subsequent steps such as amplification or detection. For example, if the sample is lysed, lysis enzymes present in the amplified sample may degrade the amplification reagents or otherwise interfere with the amplification or detection reactions, decreasing sensitivity to the sequence of interest. Further, the debris from cell lysis (including formerly intracellular enzymes) may also degrade amplification reagents, detection reagents and/or the amplification product. Certain techniques include dedicated wash steps that remove the lysis reagents and/or waste products, but washing introduces additional complexity and often user intervention.

BRIEF DESCRIPTION

In one embodiment, a method of assessing a sample is provided. In one embodiment, the method includes providing a sample assessment device including a sample application region comprising a plurality of lysis reagents; an amplification region capable of being heated to a temperature range sufficient for nucleic acid amplification; a waste region comprising an entrance coupled to the amplification region and extending away from the amplification region; a detection region spaced apart from the amplification region; and a valve separating the amplification region from the detection region. The method also includes applying a sample comprising nucleic acids to the sample application region; allowing the sample to react with the lysis reagents in a lysis reaction; allowing the sample to flow into the amplification region and react with amplification reagents for a duration of time in an amplification reaction to generate amplification products of a nucleic acid sequence of interest; allowing waste from the lysis reaction to flow into the waste region; and allowing the amplification products to flow through the valve to enter the detection region, wherein the valve is configured to be closed during the amplification reaction and open after the duration of time.

In another embodiment, a sample assessment device is provided. The sample assessment device includes a substrate including a sample application region; an amplification region; a waste region comprising an entrance fluidically coupled to the amplification region and extending away from the amplification region; and a detection region spaced apart from the amplification region. The sample assessment device also includes a valve coupled to the substrate and configured to separate the amplification region from the detection region in a closed configuration, wherein the amplification region and the valve are positioned on the sample assessment device between the sample application region and the detection region and wherein the sample assessment device is configured to permit lateral flow from the amplification region to the detection region when the valve is in an open configuration.

In another embodiment, a sample assessment system is provided. The system includes a substrate including a first region comprising a plurality of lysis reagents; a second region comprising an entrance fluidically coupled to the first region and extending away from the first region; and a third region spaced apart from the first region. The system also includes a valve separating the first region from the third region in a closed configuration to prevent lateral flow from the first region to the third region and configured to permit the lateral flow in an open configuration. The system also includes a detector configured to detect one or more signal molecules in the substrate and provide an output and a processor configured to receive the output and determine a presence or concentration of a nucleic acid sequence of interest in the biological sample based on the output.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
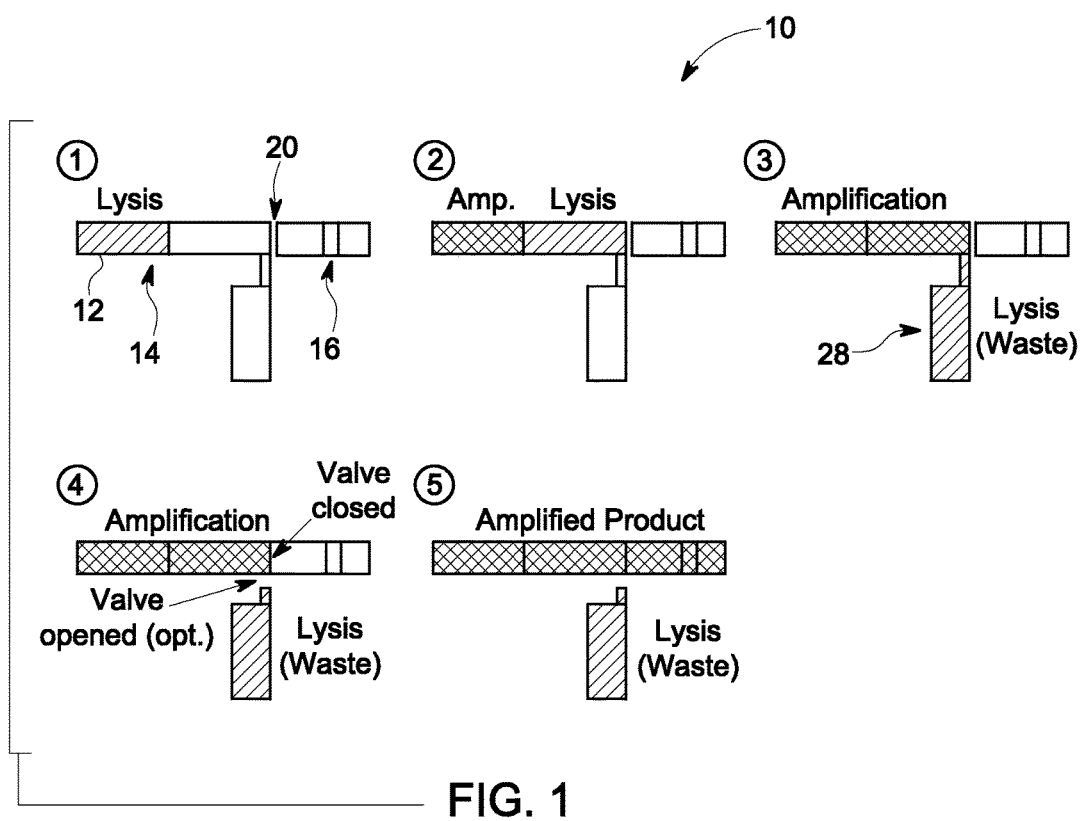
FIG. 1 is a schematic view of sample flow through a sample assessment device according to an embodiment of the disclosure.

Paper or porous substrate-based diagnostics are of growing interest to those that design, sell, and use point-of-care platforms. Such diagnostics may be low-cost, portable, and easy to use. For example, paper diagnostics have been used to detect proteins or small molecules. Implementation of paper diagnostic techniques for nucleic acid amplification is more complex. Certain techniques may involve amplification via a paper platform, but a separate end-point detection of the amplified products, e.g., by flowing the amplified material over a capture line. Accordingly, such techniques involve more steps and user effort relative to a paper diagnostics used for protein detection.

In one embodiment, a sample applied to a sample assessment device as provided herein flows through an amplification region of the device (e.g., flow through a porous substrate to encounter amplification reagents disposed in the substrate). The amplification reagents and primers specific to a target sequence of interest to produce amplification products having, or complementary to, the sequence of interest. Waste products from a sample lysis process that occurs prior to amplification are displaced downstream in the lateral flow as amplification products are generated. Accordingly, in one embodiment, waste products flow through the substrate ahead of the desired amplification products.

The sample assessment device as provided includes a diverted waste flow path for waste to decrease one or more undesired contaminants in the sample and/or in the device itself. The waste, e.g., from lysis, flows ahead of the amplification products into the waste flow path and out of the main flow path of the sample assessment device. Further, the waste is prevented from flowing downstream in the main flow path by a valve that separates downstream portions of the sample assessment device from the upstream amplification region while the amplification reaction progresses. Accordingly, the waste flow path is enriched in waste products. In one embodiment, by allowing waste to flow out of the amplification region of the sample assessment device, amplification may occur without being hindered by lysis reagents or products that may reduce the generation of amplicon or amplification products and/or may degrade such products themselves. As amplification progresses, additional amplicons are generated upstream in the main flow path as additional downstream waste is diverted into the waste flow path. Such an implementation is in contrast to techniques that do not provide an exit path for lysis products, but instead rely of wash steps to remove these products. After a suitable time period/flow volume has elapsed to permit the majority of lysis products to flow into the waste flow path and to permit sufficient amplification, the valve may be opened to permit lateral flow from the amplification reaction downstream towards a detection region. The products entering the detection region may include a reduced concentration of undesired waste contaminants, which in turn may yield improved detection and reduced signal interference.

Provided herein are techniques that may be used to amplify and detect nucleic acids in a biological sample using a lateral flow solid substrate sample assessment device. The disclosed embodiments may be used to detect a presence of a nucleic acid sequence of interest in a biological sample. The present techniques provide amplification and detection in a single substrate and reduced presence of contaminants in the amplification and detection reactions. Accordingly, amplification and detection as provided may be faster and more convenient (e.g., may include no washing steps to remove contaminants) and, thus, may be performed at the point of care or may improve workflow in a dedicated testing laboratory.

FIG. 1 is a schematic view of sample flow through a sample assessment device 10 implemented on a substrate 12 that includes a first region 14 and a second region 16 separated by a valve 20. After a lysis step (shown as step 1), a subsequent amplification step is initiated (step 2). The lysis waste products flow through the sample assessment device ahead of, or downstream of, the amplification products, as shown.

The waste products may include lysis reagents (small molecules, surfactants, membrane disruptors, lytic enzymes, etc.), the cell debris from lysis (lipids, proteins, enzymes including proteases and nucleases, and other small molecules) as well as the non-cellular components of the matrix in which the cells were delivered to the device (e.g., for blood—serum proteins and proteases, platelets, hemoglobin, etc.; or other sample matrices including sputum, or environmental contamination from forensic samples). Rather than being removed or neutralized through manual processing (column chromatography, centrifugation, washing, etc.), in the disclosed techniques, all of that separation must be done within the device without user intervention.

While the valve is closed, the waste flows into a waste region 28, as shown in step 3, by fluid displacement. The lysis waste is generated prior to amplification, as the nucleic acids of interest are not amplifiable until after release from the cells and the lysis reagents may suppress amplification. The waste is separated from the amplification reaction, and its products, via spatial/temporal fractionation of the total reaction volume. The leading fluid fraction is where lysis occurs and contains the bulk of the soluble waste products (with very little of the amplification product) and can thus be delivered to the waste pad downstream without significant loss of sensitivity. The fluid in the amplification zone can then amplify "in place" (after the amplification zone and waste zone are full of liquid) until all of the amplification reagents have been used up. The waste pad, when full, can then be disconnected (step 4) and the detection fluid path can be connected, or just the latter can occur, such that all subsequent fluid fractions that flow through to detection (step 5) contain a minimum of waste and a maximum of amplified material.

Figure 2:
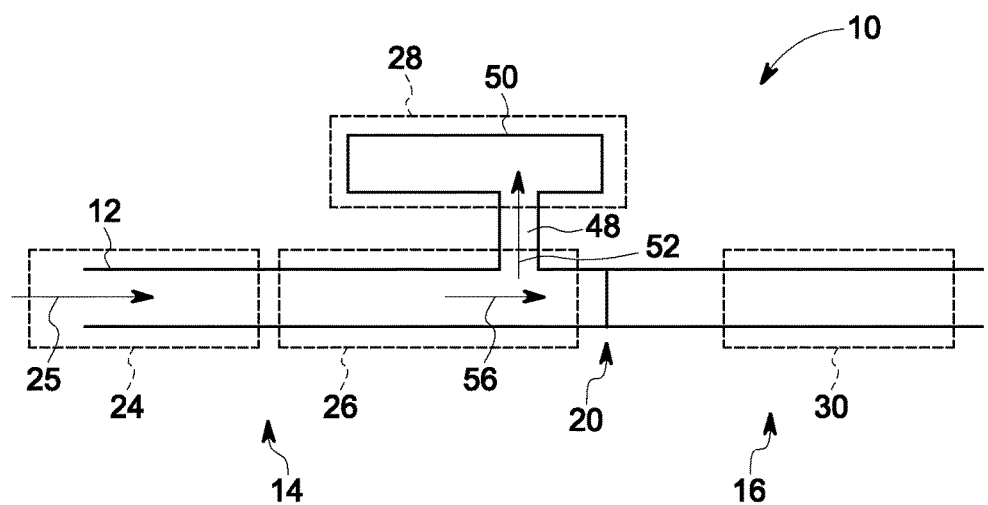
FIG. 2 is a top view of a sample assessment device according to an embodiment of the disclosure.

FIG. 2 is a top view of an example of the sample assessment device 10 including the substrate 12, e.g., a porous substrate, configured to permit lateral flow through the substrate 12. The first region 14 and the second region 16 are fluidically separated by a valve 20 in a closed configuration. That is, fluids applied to the substrate 12 cannot flow from the first region 14 to the second region 16 when the valve 20 is closed. In operation, a sample is applied to a sample application region 24 and flows in the direction of arrow 25 towards an amplification region 26, which are in the first region 14 of the substrate 12. In some embodiments, the sample application region 24 may be overlapping with or combined with the amplification region 26. That is, the sample application region 24 may have 0%, 25%, 50% or 100% overlap with the amplification region 26 in certain embodiments. In one embodiment, the substrate 12 is wet prior to or is wet concurrently with sample application to promote flow through the device 10. The substrate 12 also includes a waste region 28 that is fluidically coupled to the first region 14. When the valve 20 is closed, lateral flow to downstream detection region 30 is prevented, and products or compounds in the substrate 12 may flow into the waste region via a flow entrance 48.

The substrate 12 may include, but is not limited to, materials such as cellulose, cellulose acetate, regenerated cellulose, nitrocellulose, functionalized nitrocellulose, glass fibers, quartz fibers, polymer fibers or combinations thereof. In one embodiment, the substrate comprises cellulose. In one or more embodiments, the substrate is selected from a nitrocellulose membrane, a cellulose membrane, a cellulose acetate membrane, a regenerated cellulose membrane, a nitrocellulose mixed ester membrane, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, and any combination of two or more of the above membranes. In some embodiments, the substrate comprises modified matrices, such as pegylated cellulose, pegylated glass fiber or pegylated nitrocellulose. In some embodiments, the substrate is a porous substrate. In one embodiment, the substrate is a porous cellulose membrane. In one embodiment, the solid substrate is a porous cellulose paper, such as a cellulose substrate from GE Healthcare Life Sciences (formerly Whatman™). In one example, the cellulose substrate comprises 903-cellulose, FTA™ or FTA™ Elute. In some embodiments, the substrate 12 is a solid substrate, which is a non-water dissolvable material, which enables collection, extraction, separation, capture, detection and storage of nucleic acids followed by elution without solubilizing the material using water or aqueous buffer.

The substrate 12 may include a single layer or a plurality of layers that are joined together or otherwise coupled. In one embodiment, adjacent functional regions (e.g., the sample application region 24, the amplification region 26) may be formed from different layers that abut or overlap to fluidically couple the adjacent layers and permit lateral flow.

A "sample" or "biological sample" may include samples taken from biological subject, including biological tissue or fluid obtained from a subject. Such samples can be, but are not limited to, body fluid (e.g., blood, blood plasma, serum, sweat, wound exudate or urine), organs, tissues, biopsies, fractions, and cells isolated from, or located in, any biological system, such as mammals. Biological samples also may include sections of the biological sample including tissues (e.g., sectional portions of an organ or tissue). Biological samples may also include extracts from a biological sample, for example, nucleic acids purified from a biological fluid (e.g., blood or urine). Samples may also include unprocessed bodily fluids. For example, in one embodiment, it is envisioned that unprocessed bodily fluids may be applied directly to the porous substrate without any processing. In addition, the techniques may also be used to assess the presence of nucleic acids of interest in environmental samples, including forensic or security screening samples. In one embodiment, the techniques may be used to determine if a particular environment (e.g., a filtering system, a piping system) has been contaminated with one or more pathogens.

Although the disclosed embodiments are generally disclosed in the context of nucleic acids, it should be understood that other self-amplifying components may be tested as provided herein. Further, the nucleic acids disclosed herein may include DNA or RNA, and may be in the form of purified nucleic acids, unprocessed biological fluids that include nucleic acids or partially processed biological fluids or samples, bacterial samples, pathogenic samples, environmental samples, etc. Nucleic acids may include all forms of DNA (e.g. genomic DNA, mtDNA) or RNA (mRNA, tRNA, rRNA, small RNA, siRNA, miRNA, non-coding RNA, animal RNA, plant RNA, viral RNA or bacterial RNA), as well as recombinant RNA and DNA molecules or analogues of DNA or RNA generated using nucleotide analogues. The nucleic acids may be single stranded or double stranded. The nucleic acids may include the coding or non-coding strands. Nucleic acids may also include fragments of nucleic acids, such as naturally occurring RNA or DNA which may be recovered using the extraction methods disclosed. Nucleic acid may also refer to a portion of a nucleic acid (e.g., RNA or DNA). The extracted nucleic acids may further comprise peptide nucleic acids (PNA).

In some embodiments the sample application region 24 may include impregnated reagents, such as stabilizing reagents or cell lysis reagents. For example, the lysis reagents may lyse cells within the sample to release genomic DNA or other nucleic acid template materials. The lysis reagents, upon reaction with the sample, may generate certain waste products, such as proteins, lipids and small molecules. In addition, after the lysis is complete, the lysis enzymes themselves may be considered waste products. The lysis reagents may include, but are not limited to, guanidinium hydrochloride, guanidinium chloride, guanidinium isothiocyanate/thiocyanate, sodium thiocyanate, sodium perchlorate, sodium iodide, potassium iodide, urea, proteolytic enzymes, surfactants/membrane disruptors and/or any combination thereof. A typical anionic chaotropic series, shown in order of decreasing chaotropic strength, includes: $CCl_3COO^-$, $CNS^-$, $CF_3COO^-$, $ClO_4^-$, $I^-$, $CH_3COO^-$, $Br^-$, $Cl^-$, or $CHO_2^-$. The lysis reagent may include chaotropic substances in concentrations of from 0.1 M to 10 M, or from 1 M to 10 M. The lysis reagents may be present in the substrate 12 prior to sample application (e.g., may be impregnated in the substrate 12) or may be applied to the substrate 12. In certain embodiments, the lysis reagents may be applied concurrently with the biological sample or in a separate step.

For bacterial samples, the lysis reagents may include, for example, lytic enzymes or the biological samples may be pretreated, for example, with lytic enzymes, prior to being lysed. The lysis reagent may also comprise protease, such as serine, cysteine and metallic proteases. A protease free of nuclease may be used. A protease comprising a stabilizer, such as metallic ions, may be used. The protease may be used, upon addition, in an amount of preferably from about 0.001 IU to about 10 IU, more preferably from about 0.01 IU to about 1 IU, per ml of the whole lysis reagent. In some embodiments, the lysis reagent also includes a sufficient amount of buffer. The examples of buffers for use in the lysis reagent include tris-(hydroxymethyl) aminomethane hydrochloride (Tris-HCl), sodium phosphate, sodium acetate, sodium tetraborate-boric acid and glycine-sodium hydroxide. In some embodiments, the lysis reagent also includes a non-ionic surfactant, a cationic surfactant, an anionic surfactant, an amphoteric surfactant, and/or any combination thereof. Exemplary nonionic surfactants include, but are not limited to, t-octylphenoxypolyethoxyethanol (TRITON X-100™), (octylphenoxy)polyethoxyethanol (IGEPAL™ CA-630/NP-40), triethyleneglycol monolauryl ether (BRIJ™ 30), sorbitan monolaurate (SPAN™ 20), or the polysorbate family of chemicals, such as polysorbate 20 (i.e., TWEEN™ 20), TWEEN™ 40, TWEEN™ 60 and TWEEN™ 80 (Sigma-Aldrich, St. Louis, Mo.). Examples of cationic surfactants include cetyltrimethylammonium bromide, dodecyltrimethylammonium chloride, tetradecyltrimethylammonium chloride and cetylpyridinium chloride. The concentration of the surfactant in the lysis reagent could vary slightly among the different surfactants and depending on the components in the biological sample to be lysed. In some embodiments, the concentration of the surfactant is in a range of from about 0.01% to about 20% by weight. The lysis reagent may further comprise dithiothreitol (DTT).

The substrate 12 may also be provided with amplification reagents, including one or more primers, i.e., oligonucleotides complementary to a target sequence of interest and/or capable of hybridizing to a target sequence of interest. Sequences of interest may include sequences associated with particular pathogens, particular diseases, or particular mutations (e.g., mutations which confer disease resistance). Further, the primers may include multiple primers complementary to different regions of a single desired sequence. The amplification reagents may also include one or more polymerases and nucleotides as well as one or more appropriate buffers. The amplification reagents may be selected to work in conjunction with a particular amplification technique (e.g., loop-mediated isothermal amplification, strand displacement amplification, helicase dependent amplification, nicking enzyme amplification reaction). In one embodiment, the amplification reagents may be selected to be used in isothermal or polymerase chain reaction amplification.

In one embodiment, the substrate 12 may be provided with the amplification reagents distributed throughout the amplification region 26. In another embodiment, the substrate 12 may be provided with the amplification reagents dried on the substrate 12. An end user may wet the substrate 12 prior to use by exposing the substrate 12 to an appropriate buffer. In another embodiment, the substrate 12 may be provided with separate amplification reagents that the end user may apply to the substrate 12. The amplification reagents may be provided as separate components or as a premixed solution as part of a kit including one or more sample assessment devices.

In some applications in which the end user desires a substrate 12 for testing a particular target sequence, the primers may be provided as part of the amplification kit. That is, the amplification kit may be provided with all of the amplification reagents, including primers for a particular target sequence. An end user may purchase the amplification kit that corresponds with a particular disease, pathogen or clinical condition. In other applications, the primers may be provided separately or provided by the end user. For example, it is envisioned that the substrate 12 may be used to assess any target sequence desired by the end user. To that end, the end user may select an appropriate primer set for application to the porous substrate. In such embodiments, the end user may then apply the desired primers to the substrate 12.

Figure 3:
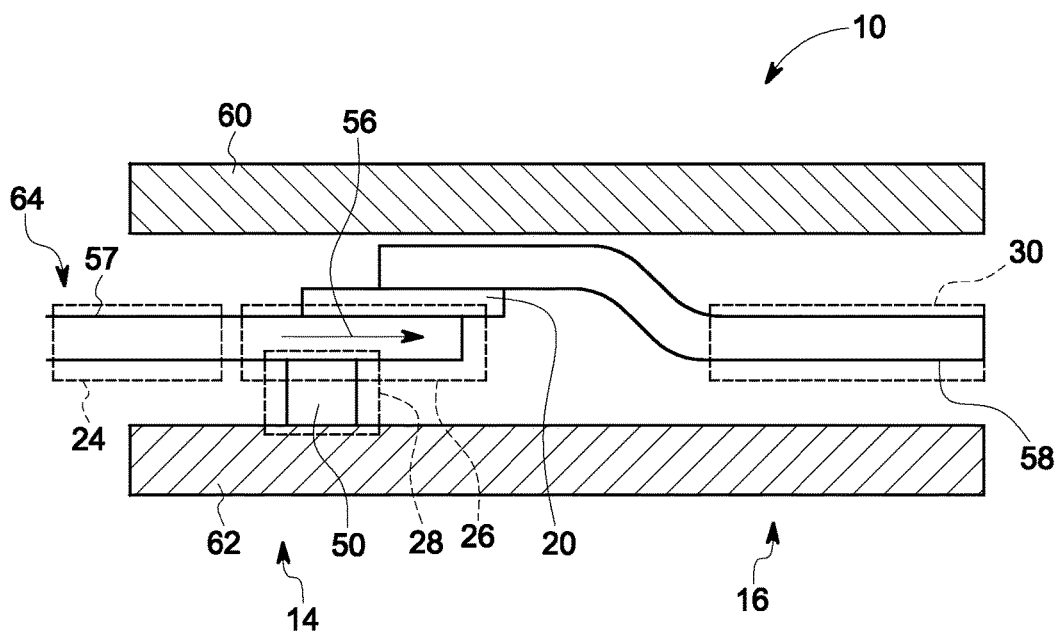
FIG. 3 is a cross-sectional view of the sample assessment device of FIG. 2.

In one embodiment, the waste region 28 may be one or more separate layers 50 of the substrate 12, as shown in the cross-sectional view of the sample assessment device 10 in FIG. 3, in direct contact with the amplification region 26 to fluidically couple the amplification region 26 to the waste region to facilitate lateral flow in the direction of arrow 52 and into the waste region 28. In another embodiment, the waste region 28 may be formed as an extending portion of the amplification region 26, e.g., the waste region 28 may be integral with the amplification region 26. When the valve 20 is closed flow in the direction of arrow 56 terminates before the detection region 30, which is in the second region 16. As shown in FIG. 3, in one embodiment, the first region 14 and the second region 16 are formed from a first layer 57 and a second layer 58 of the substrate 12 and separated by the valve 20 to prevent flow from the first region 14 into the second region 16, i.e., to prevent flow into the detection region 30.

In certain embodiments of the disclosure, the valve 20 may be a micromechanical valve, such as a check valve. In another embodiment, the valve 20 may be a hydrogel valve. In one embodiment, the hydrogel valve is configured to melt or dissolve upon exposure to a chemical (e.g., glucose concentration) or environmental condition (temperature or pH change, exposure to an electrical or magnetic field). Once melted or dissolved, the valve 20 is irreversibly positioned in the open configuration. In another embodiment, the exposure may change a porosity of the hydrogel to a more porous configuration to permit flow, whereby a less porous configuration prevented flow in the closed configuration.

The sample assessment device 10 may also include protective layers 60 and 62, between which the substrate 12 is positioned. To permit sample application, a portion of the substrate 12 (e.g., portion 64), may be extended beyond the protective layers 60 and 62 or may be otherwise accessible, e.g., via a hole or passage. When present, the protective layers 60 and 62 may be formed of generally transparent or translucent materials that permit detection in the detection zone of amplified products via optical or other techniques, as discussed herein.

In some embodiments, the substrate 12 includes an elongated strip along the main flow path and on which the sample application region 24, the amplification region 26, and the detection region 30 are all disposed. The waste region 28 may extend away from the elongated strip. The run time starting from sample application to capture of target nucleic acid may increase with increasing the length of the target nucleic acid, as the high molecular weight target nucleic acids have low mobility and migrate slowly. The separation of the nucleic acids from the sample may improve with increasing length of the elongated strip of the substrate 12. The length of the elongated strip may be optimized considering better separation as well as run time. The elongated strip may have a length in a range between 1 cm and 20 cm. In some embodiments, the elongated strip has a length less than 10 cm.

Figure 4:
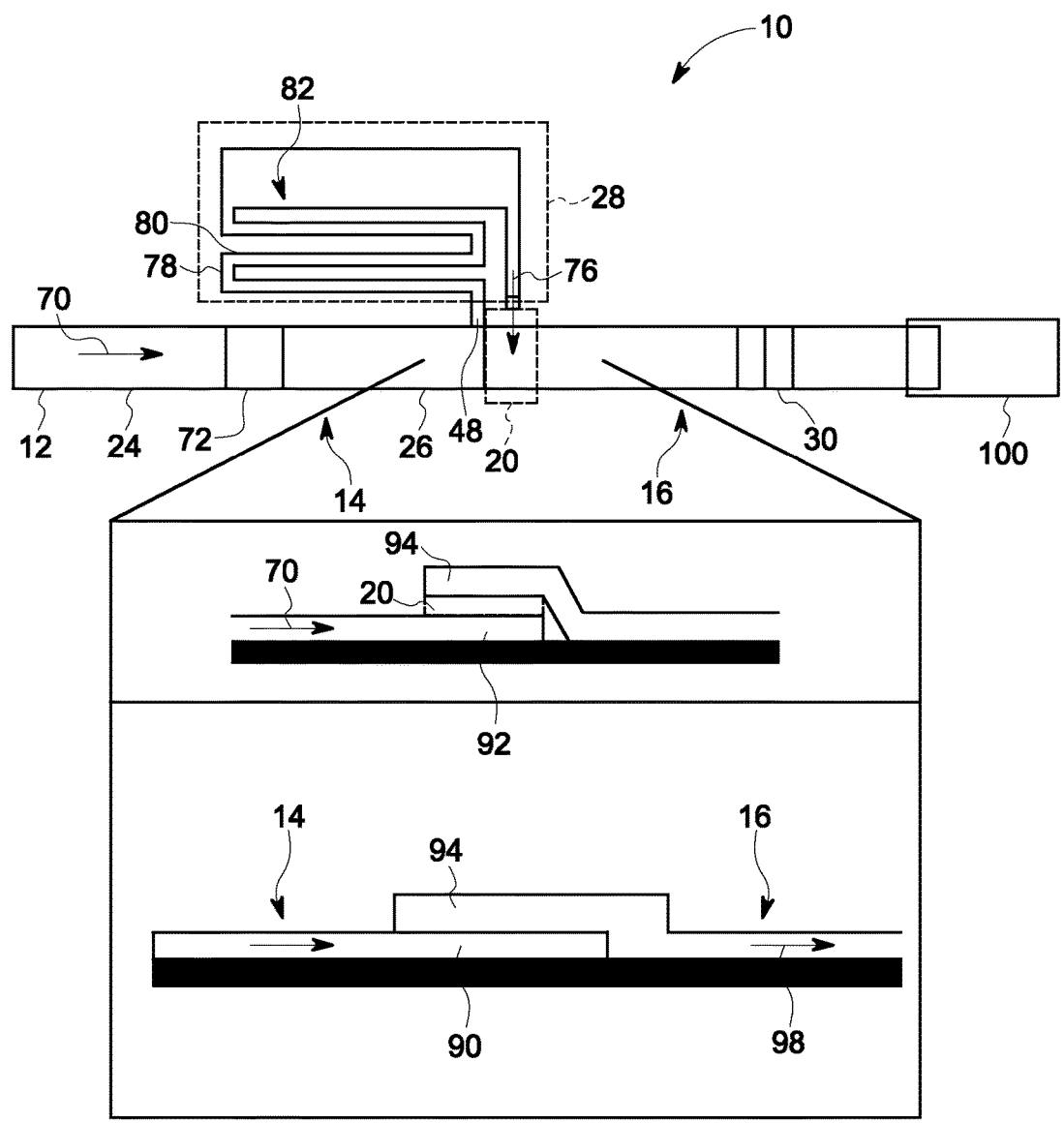
FIG. 4 is a top view and detail cross-sectional view of a sample assessment device according to an embodiment of the disclosure.

FIG. 4 is an embodiment of the sample assessment device 10 in which the valve 20 is triggered to open via flow into the waste region 28. An in-line valve 20 may provide the benefit of less complex manufacturing, because the valve 20 may be relatively simple. The sample, when applied, flows in the direction of arrow 70 through the sample application region 24, which may include lysis reagents provided as a pad or layer 72 of the substrate 12. When the sample flows into the sample application region 24, the reagents in the pad or layer, which is fluidically coupled to the sample application region, contact the sample. In this manner, a substrate 12 may be formed from less expensive materials and may include small areas of more expensive materials that are configured to include reagents as well as appropriate stabilizing or preservative materials.

Amplified products of interest are generated in the amplification region 26 and displace waste that enters the waste region 28 via entrance 48 or a portion of the waste region 28 fluidically coupled to the waste region 28 prior to the amplification flow. The waste region 28, in turn, includes a flow path that is sized and shaped so that a time to flow a terminus 76 is sufficient to permit adequate amplification. Accordingly, the waste region may include a meandering or curved path. For example, in the depicted embodiment, the waste region 28 includes a plurality of orthogonal sections 78 (i.e., orthogonal to the main flow axis along the arrow 70) and a plurality of parallel sections 80 (i.e., parallel to the main flow axis along the arrow 70). The total length of the path may be designed to permit flow of a desired duration of time to the terminus 76, with a longer path being associated with a longer duration of time. In addition, the total surface area of the waste region 28 may also be designed to permit flow of a desired duration of time to the terminus 76, with a greater surface area being associated with a longer duration of time. In one embodiment, a total surface area of the waste region 28 may be greater than a total surface area of the amplification region 26. To that end, certain sections may be thinner or thicker than other sections and/or be made from materials with different porosities, capillary forces and retention volumes. In another embodiment, the waste region 28 may also include a migration modifier to facilitate slower or faster flow to control timing of valve opening.

The terminus 76 is fluidically coupled to the valve 20 such that flow to the terminus 76 triggers opening of the valve 20. For example, the valve 20 may be a chemical valve that is configured dissolve upon contact with a particular compound. In one embodiment, the valve 20 may be a hydrogel valve configured to open at a particular pH. Flow through the terminus 76 to the valve 20 at the particular pH triggers the opening. As shown in the detail views, the valve 20 separates an end 92 of the first region 14 from an end 94 of the second region 16. When the valve is removed (e.g., by micromechanical actuation or chemical dissolving), the two ends (e., end 92 and 94) come into direct contact to fluidically couple and permit flow from the first region 14 to the second region 16 in the direction of arrow 98. The flow may then progress through the detection region 30 and, in certain embodiments, to a terminal pad 100.

In the depicted embodiment, the entrance 48 and the terminus 76 are positioned relatively close together. That is, a distance between the entrance 48 and the terminus 76 may be less than a total length of a waste path through the waste region 28, e.g., the distance between the entrance 48 and the terminus 76 may be less than 50%, 25%, or 10% of the a total length of the waste path through the waste region 28. In this manner, the entrance 48 may capture waste that is generated up to (or relatively close to) the valve 20 to facilitate greater waste removal from the flow path while still providing a sufficiently long waste path to allow the amplification reaction to progress before triggering the valve 20.

Figure 5:
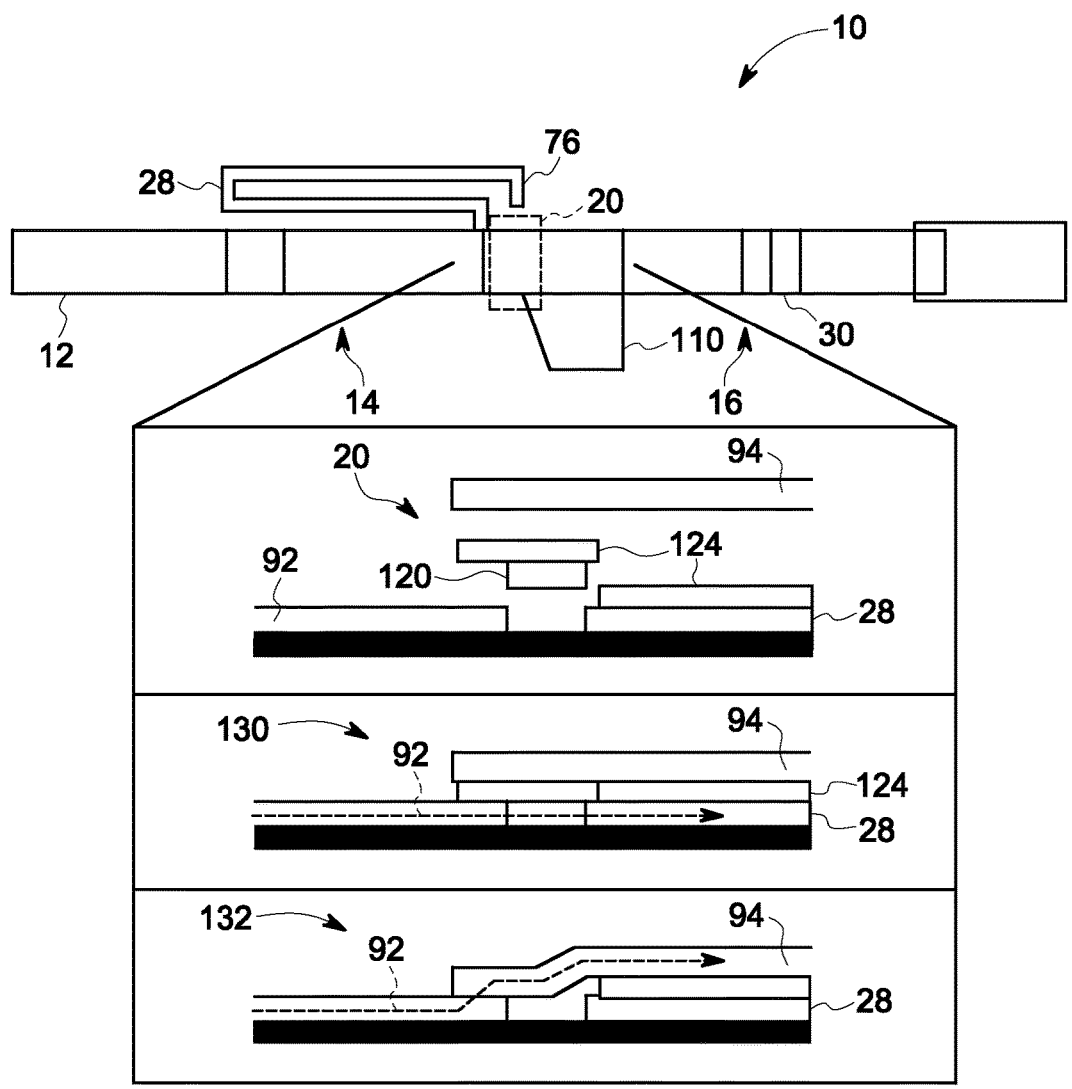
FIG. 5 is a top view and detail cross-sectional view of a sample assessment device according to an embodiment of the disclosure.

FIG. 5 is an embodiment of the sample assessment device 10 in which the valve 20 is fluidically separated from the terminus 76 of the waste region 28 (in contrast to the embodiment depicted in FIG. 4). In the embodiment of FIG. 5, the waste region 28 flows into a waste pad 110 that is separated from the valve 20. The waste pad 110, when disposed proximate to the substrate 12, may also include one or more barrier layers to prevent waste from re-entering the substrate 12. The valve 20, rather than being triggered via waste flow, is separately triggered. For example, in one embodiment, the valve 20 may be triggered to change from a closed to an open configuration by exposure to an environmental stimulus (e.g., temperature, magnetic field, electric field). The exposure may be timed to a desired amplification reaction time to permit a desired amplification product generation for detection.

As shown in the exploded cross-sectional detail of the valve 20, the valve 20 includes a hydrophilic layer and one or more hydrophobic layers 124. In the valve closed configuration 130, the hydrophilic layer 120 fluidically couples the end 92 of the first region 14 to the waste region 28, permitting lateral flow into the waste region. The hydrophobic layer/s 124 separate both the waste region 28 and the first region 14 from the second region 16. In the valve open configuration 132, the hydrophilic layer 120 of the valve 20 is removed to uncouple the first region 14 from the waste region 28 (which, in turn, may prevent backflow), and removal of one component or a portion of the hydrophobic layer 124 couples the end 92 of the first region 14 to the end 94 of the second region 16, which in turn couples the amplification region 26 to the detection region 30. A component or portion of the hydrophobic layer 124 remains in place after the valve 20 is open to isolate the waste region 28 from the end 94 of the second region 16 and, in turn, the detection region 30 While the depicted embodiments are illustrated with a single waste region 28, it should be understood that the substrate 12 may include two or more waste regions 28.

Figure 6:
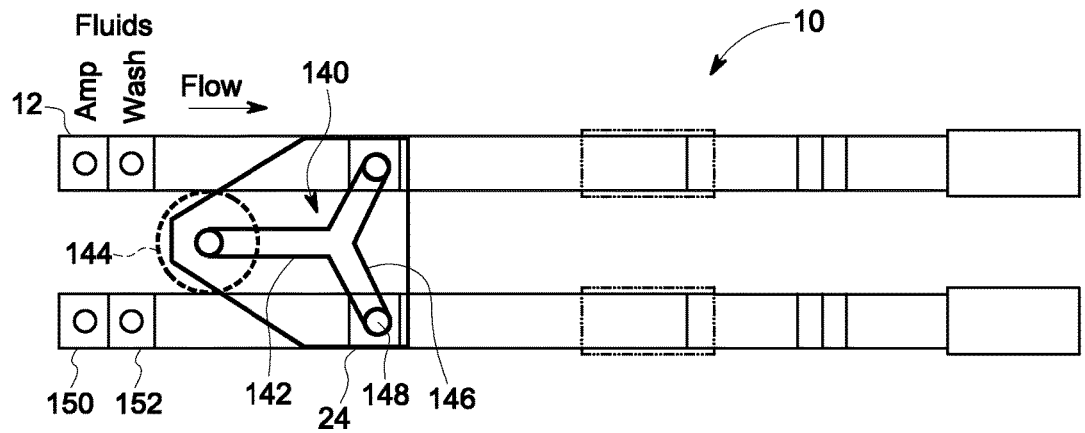
FIG. 6 is a top view of sample assessment devices including parallel capillary sample loading according to an embodiment of the disclosure.

The sample assessment device 10 as provided herein may be used in conjunction with various sample application techniques. As shown in FIG. 6, a capillary tube 140 may be used to apply a sample one or more sample assessment devices 10. The capillary tube 140 includes a sample input tube 142 forming an input passage 144. The sample input tube 142 may couple to one or more output tubes 146 that terminate in openings 148 that are designed to be positioned in contact with the sample application region of the substrate 12. The substrate 12 may also include fluid application regions, e.g., amplification fluid application region 150 and wash fluid application region 152. In this manner, the substrate 12 may have additional sample preparation, amplification, and wash functionality, depending on the type of sample. The capillary tube 140 allows the same sample to be placed on multiple substrates 12 substantially simultaneously for parallel assessment. In one example, the parallel assessment may include determining if different sequences of interest are present in the sample. In another embodiment, the assessment may be redundant for quality purposes.

Figure 7:
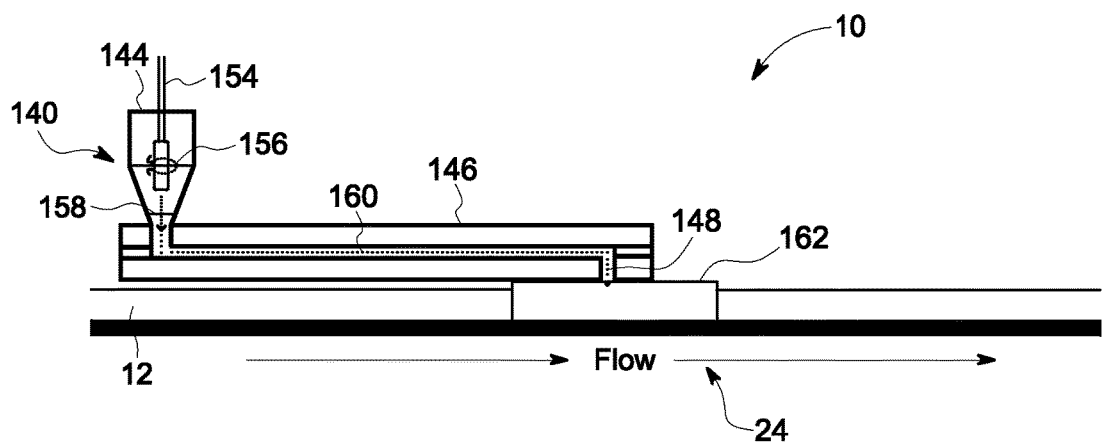
FIG. 7 is a cross-sectional view of an example of capillary loading of a sample from a swab onto a sample assessment device according to an embodiment of the disclosure.
Figure 8:
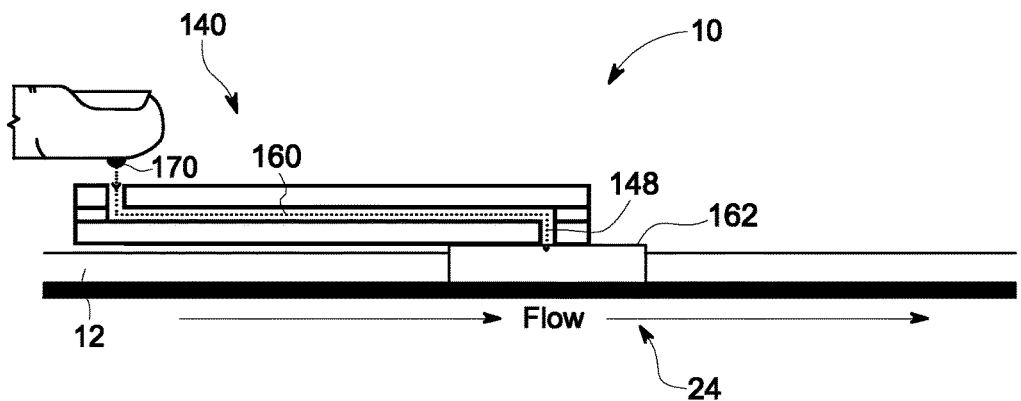
FIG. 8 is a cross-sectional view of an example of capillary loading of a blood sample onto a sample assessment device according to an embodiment of the disclosure.

FIG. 7 and FIG. 8 illustrate examples of different types of biological samples that may be used in conjunction with capillary tubes 140. In particular, depending in the type of biological sample (e.g., whole blood vs. tissue swab), different types of capillary tubes 140 may be used to receive the sample and apply the sample to the sample assessment device 10. In this manner, the sample assessment device 10 is capable of being used for different types of samples by selecting the appropriate capillary tube 140 for the desired sample. In certain embodiments, the sample assessment device 10 may be provided as a kit with one or more capillary tubes 140. In one embodiment, the kit may include packaging of a plurality of capillary tubes 140 specific for respective sample types together with one or more sample assessment devices 10. In addition, the capillary tubes 140 may be configured to receive point-of-care samples for rapid analysis.

FIG. 7 is a cross-sectional view of the sample assessment device 10 and capillary tube 140 specific for use with a sample swab 154. The capillary tube 140 includes a reservoir 156 proximate to the opening 144 to receive the sample swab 154. The capillary tube 140 also includes a seal 158 to separate the swab and any sample preparation buffers/reagents from the flow channel 160. When appropriate incubation time has elapsed to allow the sample to be eluted into the reservoir, the seal 158 may be broken to allow the sample to enter the capillary flow channel 160 and enter the sample application region 24 via the opening 148. In the depicted embodiment, the substrate includes a lytic substrate pad 162 for additional sample preparation. FIG. 8, in contrast, is illustrated with a capillary tube 140 specific for blood samples 170. In one embodiment, the blood sample 170 may be received directly from a patient (i.e., without intervening storage). The capillary tube 140 for the blood sample 170 does not include a reservoir or seal, and flow progresses directly to the lytic pad 162 of the sample application region 24 of the substrate 12.

Figure 9:
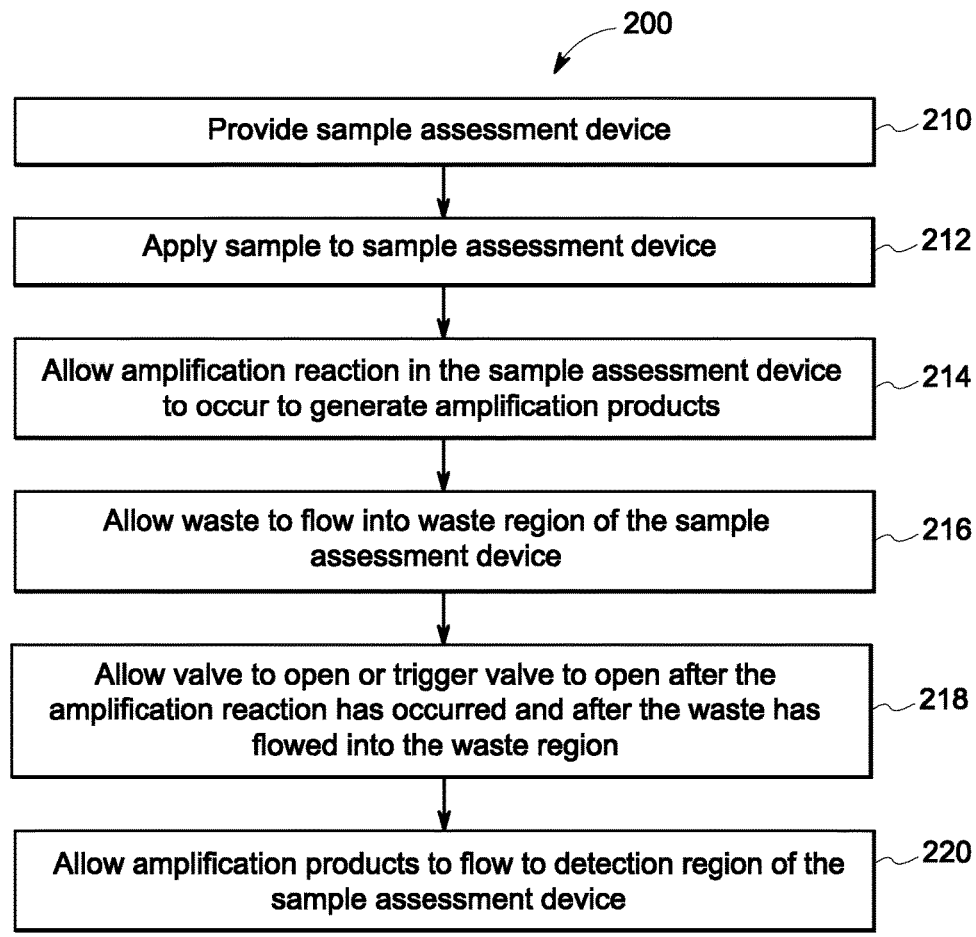
FIG. 9 is a flow diagram of a method of assessing a sample according to an embodiment of the disclosure.

FIG. 9 is a flow diagram of a sample assessment method 200. In operation, a sample assessment device is provided (block 210) and a sample is applied to the sample assessment device (block 212). The application of the sample may be manual or automatic. Further, as provided herein, the sample application may employ one or more capillary tubes (e.g., capillary tube 140, see FIG. 5). After the sample has been applied to the sample assessment device, the method 200 allows an amplification reaction to occur to generate amplification products (block 214). In addition, the method 200 allows waste from sample preparation and/or amplification to flow into a waste region of the sample assessment device (block 216). After the amplification reaction has occurred and after waste has flowed into the waste region, the valve is allowed to passively open (e.g., via waste flow that triggers to valve) or the valve is actively triggered (e.g., activation of an environmental condition or application of a chemical to the valve) (block 218). When the valve is opened, the method 200 allows the amplification products to flow into the detection region (block 220).

Figure 10:
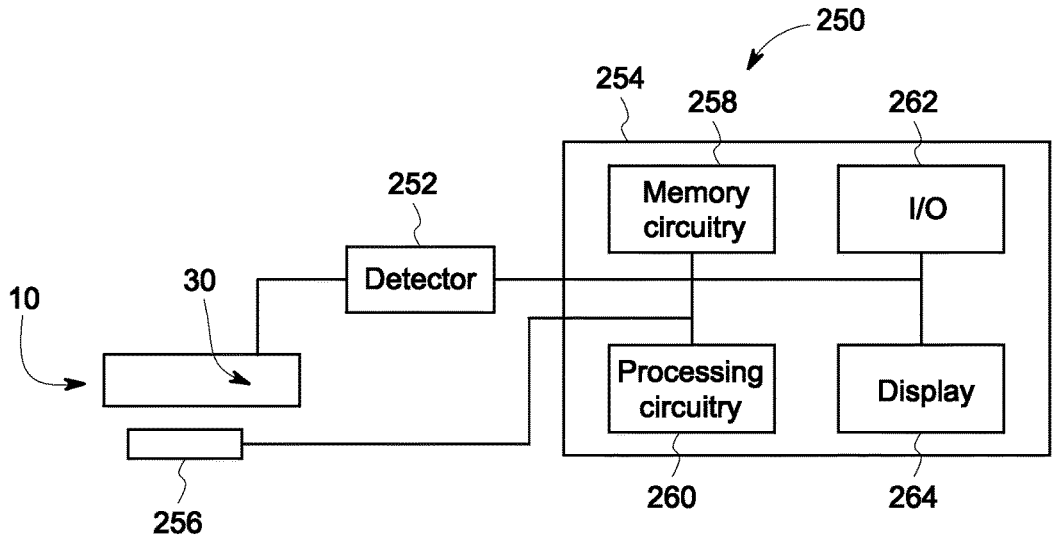
FIG. 10 is an illustration of a sample assessment system according to an embodiment of the disclosure.

FIG. 10 is a system 250 for detection of the amplified products in the detection region 30. The detection region 30 refers to an area on the sample assessment device 10 configured to facilitate detection of amplified products of the target nucleic acid sequence. In one embodiment, the amplified products are detected using nucleic acid capture probes immobilized on the substrate 12. The target nucleic acid in the amplified products of a sample is captured at the detection region 30 of the substrate 12 and thereby separated from the other non-target materials. In some embodiments, after capturing the target nucleic acids, detection probes are added to the substrate 12 and the captured nucleic acids are detected by binding with the detection probe. In some embodiments, the detection region 30 includes impregnated detection probes. While certain embodiments of the disclosed techniques permit one-step amplification and detection of amplified products in the detection region 30, it should also be understood that the migrated amplified product in the detection region 30 may be stored for later analysis.

The capture probes may include a nucleic acid that comprises at least one sequence that is complementary to at least one sequence of the target nucleic acid. In some embodiments, the nucleic acid capture probe is deoxyribonucleic acid (DNA). The nucleic acid capture probe may comprise multiple sequences that are complimentary to the DNA sequence of the target nucleic acid, such as a target DNA. The nucleic acid capture probe is applied to capture zone of a substrate, wherein the capture probe captures the target nucleic acid by hybridization.

The amplified products captured by the capture probes may be detected using signal molecules present in the amplified products, the capture probes, or primary and/or secondary detection probes. The signal generators may include a chromophore moiety, a fluorescent moiety, a phosphorescence moiety, an affinity probe, a magnetic probe, a paramagnetic probe, a plasmonic nanoparticle probe or combinations thereof. The primary detection probe may further comprise a binding moiety such as a biotin or an antibody, a streptavidin, a gold particle or combinations thereof.

The detection system 250 includes one or more sensors or detectors 252 for detecting the signal generated by the detection zone and coupled to an assessment device 254. The detector 252 may be configured to detect one or more signal molecules. For example, in certain embodiments, the detector 252 may be configured to detect optical or electrochemical signals. The sample assessment device 10 may couple to the detector 252 to facilitate detection at one or more locations along the substrate 12. The system 250 may also include heating elements 256 for heating the sample assessment device 10 to activate amplification and/or to open the valve. For example, the amplification reagents may be configured to react at particular temperatures or using particular temperature cycles. Accordingly, the system 250 may be configured to provide cyclical or isothermal heating to the substrate 12. In addition, the valve may be configured to open at particular temperatures. The heating elements 256 may be configured to open the valve after an a predetermined amount of time for amplification passes or after a predetermined amount of time after sample application, e.g., based on calibration or empirical results to achieve sufficient amplification.

The system 250 may also include computer-readable memory circuitry 258, such as magnetic, electronic, or optical storage media, for storing programs and routines executed by the device 254. The stored programs or routines may include programs or instructions for performing all or part of the present techniques. The system 250 may also include processing circuitry 260 for executing the programs or instructions, e.g., instructions to open the valve. The device 254 may also include various input/output (I/O) interfaces 262, as well as various network or communication interfaces to allow communication with user interface devices, such as a display 264, that may be used for viewing and inputting quantification information. The various network and communication interfaces may allow connection to both local and wide area intranets and storage networks as well as the Internet. The various I/O and communication interfaces may utilize wires, lines, or suitable wireless interfaces, as appropriate or desired.

Technical effects of the disclosed embodiments include rapid nucleic acid amplification and assessment. That is, the disclosed techniques facilitate amplification and detection in a single step.

This written description uses examples, including the best mode, and also to enable any person skilled in the art to practice the disclosed embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of assessing a sample comprising cells, the method comprising:
 providing a sample assessment device comprising:
  a sample application region comprising a plurality of lysis reagents;

an amplification region capable of being heated to a temperature range sufficient for nucleic acid amplification;

a waste region comprising an entrance coupled to the amplification region and extending away from the amplification region;

a detection region spaced apart from the amplification region; and a valve separating the amplification region from the detection region; wherein the sample application region, the amplification region, and the detection region are disposed on a lateral flow solid substrate, and the sample application region and the amplification region are at least partially overlapping on the lateral flow solid substrate;

applying the sample to the sample application region;

contacting the sample with the lysis reagents for lysing the cells in the sample to extract nucleic acids and generate a cell-debris, wherein the extracted nucleic acids comprise a nucleic acid sequence of interest;

amplifying the extracted nucleic acids in the amplification region by contacting the extracted nucleic acids with the amplification reagents for a duration of time to generate amplification products of the nucleic acid sequence of interest;

laterally flowing a waste, derived from the sample and the lysis reaction, into the waste region; and laterally flowing the amplification products through the valve to enter into the detection region, wherein the valve is configured to be closed during the duration of time and open after completion of the duration of time wherein the lateral flow of the waste to the waste region is effected by applying a fluid on the sample application region and laterally flowing the fluid from the sample application region via the amplification region the waste region.

2. The method of claim 1, further comprising detecting the nucleic acid sequence of interest in the detection region.

3. The method of claim 2, wherein the detection region comprises one or more nucleic acid capture probes complementary to the nucleic acid sequence of interest and wherein the detection is based on detecting the amplification products that have hybridized with the capture probes.

4. The method of claim 3. wherein the nucleic acid capture probes comprise deoxyribonucleic acids (DNA), ribonucleic acids (RNA), nucleotide analogues, or combinations thereof.

5. The method of claim 1, wherein the amplification reagents are applied to the amplification region of the substrate, impregnated in the amplification region of the substrate, or a combination thereof.

6. The method of claim 1, wherein the waste is separated from one or more of amplification reagents and the amplification product via spatial or temporal fractionation of a total amplification reaction volume on the substrate.

7. The method of claim 6, wherein the lysis reagents laterally flow into the waste region such that an amount of lysis reagents present on the amplification region of the substrate is reduced during the amplification reaction.

8. The method of claim 1, wherein the sample application region and the amplification region are fluidically isolated from the detection region when the valve is closed.

9. The method of claim 1, wherein the valve comprises a hydrogel valve.

10. The method of claim 1, wherein the valve is configured to dissolve or melt to open.

11. The method of claim 1, further comprising triggering the valve to open, after the duration of time, via application of a chemical reagent or an environmental stimulus.

* * * * *